United States Patent
Nanba et al.

(10) Patent No.: US 6,313,201 B1
(45) Date of Patent: Nov. 6, 2001

(54) MODIFIED CATALASE, A COMPOSITION THEREOF AND PROCESS FOR PREPARING THE CATALASE

(75) Inventors: Satoshi Nanba; Tomomi Suzuki, both of Niigaga-ken; Syunsuke Ohhashi; Tohru Yasukohchi, both of Kanagawa-ken, all of (JP)

(73) Assignees: Mitsubishi Gas Chemical Company, Inc.; NOF Corporation, both of Tokyo (JP)

( * ) Notice: Subject to any disclaimer, the term of this patent is extended or adjusted under 35 U.S.C. 154(b) by 0 days.

(21) Appl. No.: 09/218,892

(22) Filed: Dec. 22, 1998

(30) Foreign Application Priority Data

Dec. 25, 1997 (JP) .................................................. 9-366142

(51) Int. Cl.$^7$ ..................................................... C08L 89/00
(52) U.S. Cl. ......................... 524/17; 525/285; 525/327.4; 526/271; 526/272; 526/317.1; 526/333
(58) Field of Search ............................... 524/17; 525/285, 525/327.4; 526/271, 272, 317.1, 333

(56) References Cited

U.S. PATENT DOCUMENTS 5,081,111 * 1/1992 Akimoto et al. ..................... 525/285

FOREIGN PATENT DOCUMENTS

| 05336966 | 12/1993 | (JP) . |
| 06046847 | 2/1994 | (JP) . |
| 06141857 | 5/1994 | (JP) . |
| 07222586 | 8/1995 | (JP) . |

* cited by examiner

*Primary Examiner*—Helen L. Pezzuto (57) ABSTRACT

A composition is provided which comprises catalase modified with a copolymer (A) and a second copolymer, i.e., copolymer (B). The copolymer (A) comprises an alkenyl ether, maleic anhydride, and at least one monomer selected from the group consisting of unsaturated carboxylic acid, vinyl compound and olefin, and copolymer (B) consists of an ethylenically unsaturated monomer and a monomer selected from the group consisting of a monomer having a carboxyl group and a monomer having an acid anhydride group, or a salt of the copolymer (B).

19 Claims, 6 Drawing Sheets

FIG. 3 Storage test of modified catalase of Example 2

FIG. 4 Storage test of modified catalase of Example 3

FIG. 5
STORAGE TEST OF MODIFIED CATALASE OF EXAMPLE 4

FIG. 6
STORAGE TEST OF MODIFIED CATALASE OF EXAMPLE 5

STORAGE TEST OF MODIFIED CATALASE OF EXAMPLE 8

FIG. 10

STORAGE TEST OF COMPOSITION OF MODIFIED CATALASE OF EXAMPLE 9

MODIFIED CATALASE, A COMPOSITION THEREOF AND PROCESS FOR PREPARING THE CATALASE

This invention relates to a modified catalase which is modified with specific copolymer and is highly stable, a composition containing said modified catalase and a process for preparing the catalase.

Proteins are in general stable in vivo. However, proteins which are once isolated from living bodies and purified are so unstable that they are denatured when heated or brought into contact with acids, alkalis or organic solvents, until proteinaceous functions of their own are lost. This is due to destruction of the specific higher-order structure of protein.

Catalase is a known enzyme which catalyzes decomposition of hydrogen peroxide. As catalase is one of proteins, there is no exception.

Consequently, studies have been made for applying modified enzymes which are prepared by chemical modification of proteins with synthetic polymers and are stabilized against heat or acids, alkalis or organic solvents to fields of medical, pharmacological, engineering or agricultural sciences.

Functions to be expected to the modified proteins are: (1) disappearance of antigenicities which may cause problems when the proteins are administered as a pharmaceutical in vivo, and extension of internal retention time; (2) a missile therapy using medicines such as antibiotics or antitumor agents bound with antibodies; and (3) catalysts for bioreactors which are made soluble in organic solvents by being modified with amphipatic synthetic polymers.

As modifiers used for stabilization of enzymes, a modification of catalase, for example, with 2,4-bis(o-methoxy polyethylene glycol)-6-chloro-s-triazine is reported (Biochem. Biophys. Res. Commun. Vol. 125, No. 2, 761–766, 1984). This is, however, for the purpose of having catalase solubilized in organic solvents, and it is hard to produce a large amount of modified enzymes, because the method requires several steps.

Further examples of the other stabilized modified enzymes are a modified protease (JP 6-205675A) and a modified asparaginase (JP 5-336966A).

Catalase in itself, however, is denatured in the presence of peroxoacid salts such as sodium peroxocarbonate and sodium peroxoborate. Consequently, no catalytic action of catalase can be expected in the presence of peroxoacid salts.

The first aspect of the present invention is to provide modified catalase which can be stored with highly stability (hereinafter sometimes designates simply as stored stability) without disturbance of original properties of catalase for a long term in the presence of peroxoacid salts such as sodium peroxocarbonate and sodium peroxoborate, and can be mass-produced by simple operations.

The second aspect of the present invention is to provide a composition containing the modified catalase.

The third aspect of the present invention is to provide a process for preparing the modified catalase.

We have found that catalase which is modified by copolymers having at least both a polyoxyalkylene group and an acid anhydride group in the same molecule maintains stability for a long term without losing stability even in the presence of peroxoacid salts such as sodium peroxocarbonate and sodium peroxoborate.

In the accompanying drawings.

The first aspect of the invention is a modified catalase which is characterized by being modified with a copolymer (A) which comprises (a) one or more alkenyl ether of the formula (1) mentioned below, (b) maleic anhydride and (c) at least one monomer selected from the group consisting of an unsaturated carboxylic acid, vinyl compound and olefin, and has a molar ratio of the above (a), (b) and (c) of 5–60:20–90:0–30, respectively, (1)

wherein Z is a residue of a compound having 2 to 8 hydroxyl groups, AO is one or more oxyalkylene groups having 2 to 18 carbon atoms, and may be in block or random addition when two or more of them are in addition at the same time, $R^1$ is an alkenyl group having 2 to 5 carbon atoms, $R^2$ is a hydrocarbon or acyl group having 1 to 24 carbon atoms, a and b are each 0 to 1000, m is 1 to 7 and a+bm is 1 to 1000.

The modified catalase is stabilized against peroxoacid salts.

The second aspect of the invention is a composition of the modified catalase which is characterized by containing the modified catalase of the first aspect and a copolymer (B) which is made from an ethylenically unsaturated monomer and either a monomer having a carboxyl group or a monomer having an acid anhydride group. Salts of the copolymer (B) may be used, as the (B).

The third aspect of the invention is a process for preparing the modified catalase mentioned above by modifying a catalase with the copolymer (A) above mentioned at a temperature range from −5° C. to 10° C. and a pH range from 6 to 10.

In the formula (1), the compound having 2–8 hydroxyl groups for the residue Z are, for example, glycols such as ethylene glycol, propylene glycol, butylene glycol, hexylene glycol, styrene glycol, alkylene glycols of $C_{8-18}$ and neopentyl glycol; polyhydric alcohols such as glycerin, diglycerin, polyglycerin, trimethylolethane, trimethylolpropane, 1,3,5-pentanetriol, erythritol, pentaerythritol, dipentaerythritol, sorbitol, sorbitane, sorbite, a condensation product of sorbitol and glycerin, adnitol, arabitol, xylitol and mannitol, and partial etherification compounds or partial esterification compounds of the polyhydric alcohols; saccharides such as xylose, arabinose, ribose, rhamnose, glucose, fructose, galactose, mannose, sorbose, cellobiose, maltose, isomaltose, treharose, sucrose, raffinose, gentianose and melezitose, and etherification compounds or esterification compounds of the saccharides; and phenols such as catechol, rezorcinol, hydroquinone and phloroglucine. Preferences are glycols and polyhydric alcohols, more preferably ethylene glycol, propylene glycol, butylene glycol and glycerin.

The oxyalkylene groups having 2 to 18 carbon atoms represented by AO are an oxyethylene group, oxypropylene group, oxybutylene group, oxytetramethylene group, oxystyrene group, oxydodecylene group, oxytetradodecylene group, oxyhexadecylene group and oxyoctadecylene group. Preferable oxyalkylene group having 2 to 18 carbon atoms represented by a symbol AO is one having 2 to 4 carbon atoms, more preferably an oxyethylene group, oxypropylene group, oxybutylene group and oxytetramethylene group. One or two or more of these groups may be simultaneously added. In case where two or more are in addition at the same time, they are in block addition or random addition. Preference is the oxyalkylene group in which the oxyalkylene group ($-C_2H_4O-$) is 20% by weight.

In the formula AO, each of symbols a and b is average addition moles of oxyalkylene groups having 2 to 18 carbon atoms. The oxyalkylene groups having 2 to 18 carbon atoms are essential for increasing affinity between the copolymer (A) and the catalase and stability of the catalase. "a+bm" is preferably 1 to 500, more preferably 1 to 200, in order to obtain the desired modified catalase. When a+bm exceeds 1000, a weight ratio of maleic anhydride unit in the copolymer is decreased. As a result, a reaction against an amino group in lysine unit or amino terminal group in catalase hardly occurs until the desired modified catalase can not be obtained.

Alkenyl groups having 2 to 5 carbon atoms represented by $R^1$ are a vinyl group, allyl group, methacryl group, 1,1-dimethyl-2-propenyl group and 3-methyl-3-butenyl group. Alkenyl groups having 3 to 5 carbon atoms, such as allyl group and methallyl group, are preferable.

Hydrocarbon groups having 1 to 24 carbon atoms represented by $R^2$ are, for example, alkyl groups having 1 to 24 carbon atoms and aromatic hydrocarbons having 1 to 24 carbon atoms. Alkyl groups having 1 to 24 carbon atoms are methyl, ethyl, propyl, isopropyl, butyl, isobutyl, tert-butyl, pentyl, isopentyl, hexyl, isoheptyl, 2-ethylhexyl, octyl, isononyl, decyl, dodecyl, isotridecyl, tetradecyl, hexadecyl, isocetyl, octadecyl, isostearyl, oleyl, octyldodecyl, dococyl and decyltetradecyl groups. Aromatic hydrocarbons having 1 to 24 carbon atoms are, for example, benzyl, tolyl, butylphenyl, dibutylphenyl, octylphenyl, nonylphenyl, dodecylphenyl, dioctylphenyl and dinonylphenyl groups.

Acyl groups having 1 to 24 carbon atoms represented by $R^2$ are acyl groups originated from acetic acid, propionic acid, butyric acid, isobutyric acid, caprilic acid, 2-ethylhexanic acid, isononanoic acid, capric acid, lauric acid, myristic acid, palmitic acid, isopalmitic acid, stearic acid, isostearic acid, arachic acid, behenic acid, palmitoleic acid, oleic acid, linoleic acid, linolenic acid, erucic acid, benzoic acid, hydroxybenzoic acid, cinnamic acid and gallic acid. Preferences are hydrocarbons and acyl groups having 1 to 4 carbon atoms.

One or two or more alkenyl ethers represented by the formula (1) can be used.

It is essential for the polymer (A) to have an acid anhydride structure in order to sufficiently bind it with catalase, the copolymer (A) comprising (a) alkenyl ether represented by the formula (1), (b) maleic anhydride and (c) at least one monomer selected from the group consisting of unsaturated carboxylic acids, vinyl compounds and olefins in a molar ratio of 5–60:20–90: 0–30, preferably 20–60:40–70:0–20, respectively.

Representative examples of the monomer selected from the group consisting of unsaturated carboxylic acids, vinyl compounds and olefins are unsaturated carboxylic acids such as acrylic acid, methacrylic acid, itaconic acid and crotonic acid, aromatic vinyl compounds such as styrene and methylstyrene, vinyl halides such as vinyl chloride and vinylidene chloride, olefins such as isobutylene and diisobutylene, and vinyl acetate.

When the monomers (c) are contained in the copolymer (A), an amount of these monomers (c) should not exceed 30 molar percent on the basis of the total of the monomers for the copolymer (A). Large ratio of these monomers (c) decreases each content of polyoxyethylene chain and acid anhydride which are necessary for modification of catalase, until not enough modification of catalase is effected.

The copolymer (A) can readily be obtained by conventionally copolymerizing alkenyl ether represented by the formula (1) with maleic anhydride in the presence of radical copolymerization catalysts (polymerization initiators). If desired, the monomer (c) is added, and then three components may be copolymerized. Furthermore, the monomer (c) may be polymerized after radical copolymerization between alkenyl ether represented by the formula (1) and maleic anhydride is effected.

The radical copolymerization catalysts may be anyone which are familiar in the art. Examples are organic peroxides such as lauroyl peroxide, tert-butylperoxy-2-ethylhexanoate, benzoyl peroxide and tert-butyl perbenzoate, inorganic peroxides such as hydrogen peroxide and potassium persulfate, azo and diazo compounds such as azobisisobutyronitrile and diazoaminoazobenzene, aromatic sulfinic acid, alkyl mercury and alkyl lead.

The copolymer (A) may have various forms depending on varieties of radical copolymerization catalysts, conditions for polymerization and alkenyls represented by the formula (1). Weight average molecular weight is $0.5 \times 10^4$ to $200 \times 10^4$ or so, more preferably $0.5 \times 10^4$ to $15 \times 10^4$ or so.

In case where alkenyl ethers represented by the formula (1) in which numbers of an oxyethylene group are comparatively large is used, solid copolymer can usually be obtained at normal temperature or ambient temperature.

Raw material catalase which is used in the present invention may be that obtained from animals, plants and aerobic cells of microorganisms, and are not limitative. Commercial products can also be used as they are.

The modified catalase of the present first invention is obtained by allowing the copolymer (A) hereinbefore to react with catalase. An amino group in a lysine unit or terminal amino group in catalase is bound with the copolymer (A).

Ratio of the above copolymer (A) to the catalase varies depending on respective numbers of the amino group in the lysine unit and the terminal amino group in the catalase and acid anhydride content in the copolymer, and is not specified. An amount of the copolymer (A) is preferably about 20 to 1,000 parts, more preferably about 50 to 1,000 parts by weight to 100 parts by weight of the catalase. If an amount of the copolymer (A) is too small compared with number of the amino group, modification ratio is decreased accordingly until stability of catalase becomes insufficient. On the other hand, if an amount of the copolymer (A) is too much, modification ratio of catalase becomes too large until desired activity of catalase greatly decreases. In both cases, these products can not be used in practice.

Catalase can be modified with the copolymer (A) by means of a reaction between the catalase and the copolymer (A), said reaction being known. Namely, an aqueous solution of catalase is mixed with the copolymer (A). If the copolymer (A) is insoluble or slightly soluble in water, preference is that the copolymer (A) is previously dissolved in water-miscible organic solvents such as acetone and toluene, before the resulted solution is mixed with an aqueous solution of catalase.

Some copolymer encounters difficulty in that ratio of modification of catalase is decreased and desired storage stability of the modified catalase can not be obtained, if the total amount of the copolymer is mixed with catalase at once. Consequently, in order to avoid such difficulty, it is preferable to add the copolymer (A) divisionally to the aqueous solution of catalase. Number of the division is variable depending upon a composition and amount of the copolymer (A), usually preferably 2 to 5 times, but not limited to thereto. An amount of addition of the divided copolymer (A) may be different each time, but may be the same. Furthermore, the total amounts of the copolymer (A) may be mixed at one time with catalase.

The reaction is performed under slightly acidic or alkaline conditions, preferably at pH 6 to 10, most preferably at pH 7 to 9. When the reaction is effected under the strong acidic conditions, reactivity of the lysine residue in the catalase is decreased until the modification rate is decreased. When the reaction proceeds under the strong alkaline conditions, hydrolysis of the acid anhydride group of the copolymer (A) prevails until the modification rate is decreased.

Reaction temperature is preferably at −5 to 10° C., more preferably at 0 to 10° C., in practice. If the reaction temperature is too high, activity of catalase in the modification process decreases. Furthermore, a hydrolytic reaction of an acid anhydride group prevails over a reaction between an amino group of the catalase and an acid anhydride group, with the result that the modification rate is decreased. On the other hand, if the reaction temperature is too low, the copolymer (A) is solidified, so that it can not be used in practice.

The modified catalase of the present first invention is pasty which is difficult to use, depending on a composition of copolymer (A). In this case, inorganic salts such as sodium sulfate or sodium chloride which do not deteriorate storage stability of the modified catalase are added to the pasty modified catalase before use, for an easier treatment, until the modified catalase is preferably in the powdery form.

In order to increase further storage stability of the modified catalase of the above first invention, a composition of the modified catalase is provided. The composition contains the modified catalase of the above first invention and a copolymer (B) consisting of an ethylenically unsaturated monomer and either a monomer having a carboxyl group or a monomer having an acid anhydride group. Salts of the copolymer (B) may also be used.

The ethylenically unsaturated monomer for the copolymer (B) is, for example, ethylenic hydrocarbons (olefins) such as ethylene, propylene, butylene and isobutylene and aromatic vinyl compounds such as styrene and α-methylstyrene. Preferences are isobutylene and styrene, more preferably isobutylene.

Monomers having a carboxyl group or acid anhydride group for the copolymer (B) are acrylic acid, methacrylic acid, itaconic acid, crotonic acid, maleic acid and maleic anhydride. Preferences are maleic acid and maleic anhydride.

In the copolymer (B), a ratio of the ethylenically unsaturated monomer to the monomer having a carboxyl group or acid anhydride group or salts thereof is, usually 10–80:20–90, preferably 30–70:30–70, in mole.

Commercially available products of the copolymer (B) can also be used. Preferable copolymer (B) is a copolymer of isobutylene and maleic anhydride, which has $5 \times 10^4$ to $17 \times 10^4$ of number average molecular weight.

Salts of the copolymer (B) are, for example, alkali metal salts such as lithium, sodium and potassium salts; amine or ammonium salts such as methylamine, dimethylamine, ethylamine, monoethanolamine, diethanolamine, triethanolamine and methylethanolamine salts. Preferences are alkali metal salts and ammonium salts.

A composition of the modified catalase having extremely good stability can be obtained by mixing preferably 0.1 to 1000 parts by weight, more preferably 1 to 500 parts by weight, most preferably 5 to 250 parts by weight of the copolymer (B) with 100 parts by weight of the aforesaid modified catalase of the present first invention.

Any process known per se is carried out for producing the composition of modified catalase. One of the processes is that an aqueous solution of the modified catalase hereinbefore and the copolymer (B) are directly mixed. Alternatively, an aqueous solution where the copolymer (B) has been dissolved in water may be mixed with the aqueous solution of the modified catalase above mentioned. When the copolymer (B) is hardly soluble or insoluble in water, a solution in which the copolymer (B) has previously been dissolved in water-miscible organic solvents such as acetone or toluene may be mixed with the aqueous solution of the modified catalase mentioned hereinbefore.

A gummy, powdery or particle composition of the modified catalase can be obtained by distilling off the water and organic solvents from the above mixture. If necessary, the powder may be subjected to size enlargement to prepare granules.

The present invention is explained in details by the following preparation examples and examples, but is not limited thereto.

PREPARATION EXAMPLE 1

Production of copolymer (A)

The following compounds were dissolved in toluene (1 lit.) and subjected to a polymerization reaction by heating at $80\pm2°$ C. for 7 hours under a nitrogen gas atmosphere.

| | |
|---|---|
| $CH_2=CHCH_2O(C_2H_4O)_{11}CH_3$ | 556 g (1.0 mole) |
| Maleic anhydride | 103 g (1.05 mole) |
| tert-butyl peroxy-2-ethyl hexanoate | 4.3 g (0.02 mole) |

Toluene and unaltered maleic anhydride were distilled off under reduced pressure of 10 to 30 mmHg at $100\pm10°$ C. to obtain 528 g of copolymer (A) No. 1.

The obtained copolymer (A) No. 1 was brownish transparent liquid having 206.2 cSt of kinematic viscosity at 100° C. and 182.0 KOH mg/g of saponification value.

PREPARATION EXAMPLE 2

The following compounds were dissolved in toluene (2 lit.) and subjected to polymerization reaction by heating at $80\pm2°$ C. for 9 hours under a nitrogen gas atmosphere.

| | |
|---|---|
| $CH_2=C(CH_3)CH_2O(C_2H_4O)_{44}CH_3$ | 2022 g (1.0 mole) |
| Maleic anhydride | 103 g (1.05 mole) |
| tert-butyl peroxy-2-ethyl hexanoate | 10.8 g (0.05 mole) |

Toluene and unaltered maleic anhydride were distilled off under reduced pressure of 10 to 30 mmHg at 110±10° C. to obtain 928 g of copolymer (A) No. 2.

The obtained copolymer (A) No. 2 was white solid at 25° C. having 36.1 KOH mg/g of saponification value.

PREPARATION EXAMPLE 3

Preparation example 2 was repeated except that alkenyl ethers shown in table 1 and maleic anhydride, monomers (c) and catalysts shown in table 2 were used in the mole ratios shown in tables 1 and 2, to produce copolymer (A) Nos. 3 to 8.

Weight-average molecular weights, saponification values, states of matter and solubilities in organic solvents of the copolymer (A) Nos. 3 to 8 are shown in table 3.

TABLE 1

Composition (1) of copolymer (A)
Alkenyl ether represented by the formula (1)

| Copolymer (A) | Structure | Mole | EO content (wt %) |
|---|---|---|---|
| No. 1 | $CH_2=CHCH_2O(C_2H_4O)_{11}CH_3$ | 1.0 | 100 |
| No. 2 | $CH_2=C(CH_3)CH_2O(C_2H_4O)_{44}CH_3$ | 1.0 | 100 |
| No. 3 | $CH_2=CHCH_2O(C_2H_4O)_{20}C_4H_9$ | 0.5 | 100 |
|       | $CH_2=C(CH_3)CH_2O(C_2H_4O)_{20}(C_3H_6O)_{10}C_{12}H_{25}$ | 0.5 | 60 |
| No. 4 | $CH_2=CHCH_2O(C_3H_6O)_5(C_2H_4O)_{15}CH_3$ | 1.0 | 69 |
| No. 5 | $CH_2=CHCH_2O(C_3H_6O)_{50}(C_2H_4O)_{50}C_{18}H_{37}$ | 0.9 | 43 |
| No. 6 | $CH_2=CHCH_2O(C_2H_4O)_{45}C_4H_9$ | 0.9 | 100 |
| No. 7 | $CH_2=CHCH_2O\{(C_2H_4O)_5(C_4H_8O)\}CH_3$ | 0.1 | 75 |
|       | $CH_2=CHCH_2O(C_2H_4O)_{20}(C_3H_6O)_{20}COC_{17}H_{35}$ | 0.1 | 43 |
|       | $CH_2=CHCH_2O(C_2H_4O)_{33}CH_3$ | 0.8 | 100 |
| No. 8 | $CH_2OCH_2CH=CH_2$<br>$\|$<br>$CHO(C_2H_4O)_{12}CH_3$<br>$\|$<br>$CH_2O(C_2H_4O)_{12}CH_3$ | 0.5 | 100 |
|       | $CH_2=CHCH_2O(C_2H_4O)_{33}CH_3$ | 0.5 | 100 |

Note:
{ } indicates a random addition product.
EO: oxyethylene group

TABLE 2

Composition (2) of copolymer (A)

| Copolymer (A) | Maleic anhydride Mole | Monomer (c) Name | Monomer (c) Mole | Catalyst Name | Catalyst Mole |
|---|---|---|---|---|---|
| No. 1 | 1.05 | — | — | tBEH | 0.02 |
| No. 2 | 1.05 | — | — | tBEH | 0.05 |
| No. 3 | 1.05 | — | — | LPO | 0.02 |
| No. 4 | 1.0 | — | — | tBEH | 0.03 |
| No. 5 | 1.0 | Diisobutylene | 0.1 | tBEH | 0.1 |
| No. 6 | 1.0 | Styrene | 0.1 | tBEH | 0.03 |
| No. 7 | 1.0 | — | — | BPO | 0.1 |
| No. 8 | 1.0 | — | — | tBEH | 0.01 |

Note:
BPO: benzyl peroxide
LPO: lauroyl peroxide
tBEH: t-butyl peroxy-2-ethyl hexanoate

TABLE 3

Specificities of copolymer (A)

| Copolymer (A) | Weight-average molecular weight | Saponification value | States 20° C. | States 100° C. | Solubility Water | Solubility Acetone | Solubility Benzene |
|---|---|---|---|---|---|---|---|
| No. 1 | 20,000 | 182.0 | liquid | liquid | soluble | soluble | soluble |
| No. 2 | 83,000 | 36.1  | solid  | liquid | soluble | soluble | soluble |
| No. 3 | 48,000 | 81.5  | liquid | liquid | soluble | soluble | soluble |
| No. 4 | 32,000 | 101.5 | liquid | liquid | soluble | soluble | soluble |
| No. 5 | 25,000 | 70.6  | liquid | liquid | soluble | soluble | soluble |
| No. 6 | 18,000 | 100.6 | solid  | liquid | soluble | soluble | soluble |
| No. 7 | 14,000 | 73.5  | liquid | liquid | soluble | soluble | soluble |
| No. 8 | 12,000 | 76.1  | solid  | liquid | soluble | soluble | soluble |

Modified catalases in the following examples were prepared by modifying the catalase ("Ascsuper": trade name, product of Mitsubishi Gas Chemical Co., Inc.) with copolymers (A) Nos. 1 to 8 obtained in the above preparation examples.

Activities of the obtained modified catalases were assayed in such a manner that the modified catalase is allowed to react at 30° C. with hydrogen peroxide which is contained in an aqueous hydrogen peroxide solution at the designated concentration, the remained hydrogen peroxide is measured by potassium iodide-potassium thiosulfate titration and catalase activity is calculated from the decomposed amount of hydrogen peroxide. One unit of catalase is defined as catalase activity which decomposes $1\mu$ mole of hydrogen peroxide per minute.

Storage Test and its Result of Unmodified Catalase:

Unmodified catalase 100,000 units and sodium peroxycarbonate 100 g were mixed uniformly, and allowed to store in thermostats kept at 30° C., 40° C. and 50° C., respectively. Catalase activities were assayed (hereinafter designate as the remaining activities). Remaining relative catalase activities which are percentages of the remaining activities to initial activities of modified catalases were calculated from the remaining activities.

Figure 1:
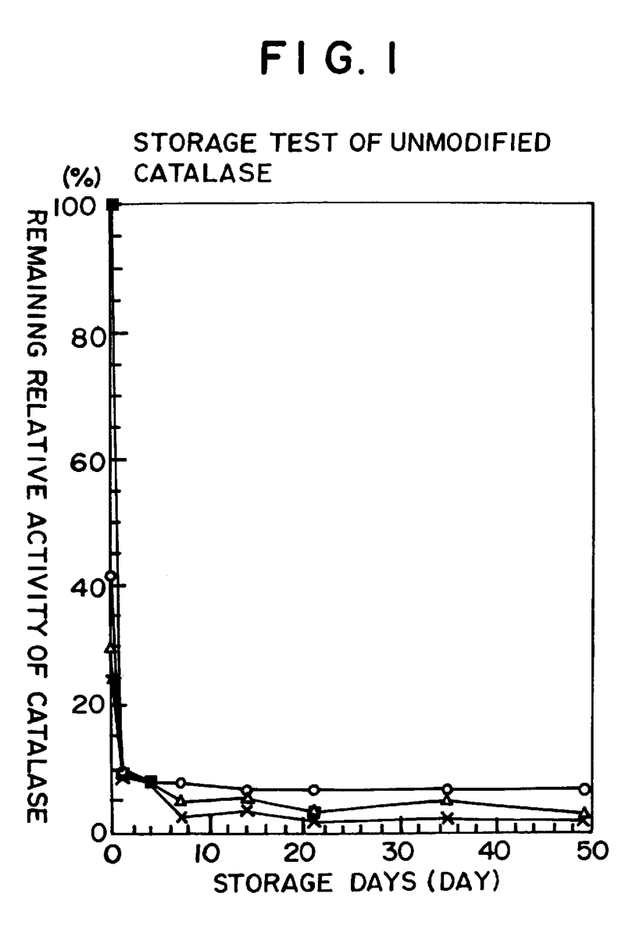
FIG. 1: Result of storage test of unmodified catalase.

Results are shown in FIG. 1.

Storage Test Method of the Modified Catalase of the Present Invention:

Modified catalase 100,000 units were added to sodium peroxocarbonate 100 g, and mixed well to obtain compositions for evaluation of stability. The mixtures were allowed to store in thermostats kept at 30° C., 40° C. and 50° C., respectively.

Remaining activities were assayed at 6 hours, 1 day, 4 days, 1, 2, 3, 5 and 7 weeks after initiating the storage, and remaining relative catalase activities were calculated therefrom.

The storage test method of the modified catalase of the present invention was performed as same as the above storage test method of modified catalase of the present invention.

In FIG. 1 to FIG. 11, lines connected with the open circle (-○-), lines connected with the open triangle (-Δ-) and lines connected with the crosses (-x-) indicate "storage at 30° C.", "storage at 40° C." and "storage at 50° C.", respectively.

EXAMPLE 1

Catalase 5 g was dissolved in 100 g of borate buffer pH 9.0 and the solution of catalase was maintained at 3° C.

Fine powder (2.5 g) of copolymer (A) No. 1 obtained in the preparation example hereinbefore was added to the solution of catalase. The mixture was stirred at 3±1° C. for 30 minutes. Then, the fine powder (2.5 g) of copolymer (A) No. 1 obtained in the preparation example hereinbefore were added to the mixture. Water was distilled off at 25° C. in vacuo to obtain modified catalase 9.2 g.

The thus obtained catalase was so pasty that sodium sulfate 325 parts by weight was added to the modified catalase 100 parts by weight to obtain the powdered modified catalase. The powdered catalase was used for Storage tests.

| Borate buffer (pH 9.0) | |
|---|---|
| Aqueous solution of 0.05 M borate | 90 ml |
| Aqueous solution of 0.2 M borate-0.05 M sodium chloride | 10 ml |

Solution obtained by mixing the above two solutions.

Borate buffers used in the following examples are the same as above.

Catalase activity of the obtained modified catalase was assayed to find that 1/5 activity of the original catalase was maintained.

Mixtures obtained by uniformly blending the modified catalase 100,000 units and sodium peroxocarbonate 100 g were tested for storage in thermostats kept at 30° C., 40° C. and 50° C., respectively. Activities of catalase during the storage were assayed and remaining relative activities of catalase were calculated.

Figure 2:
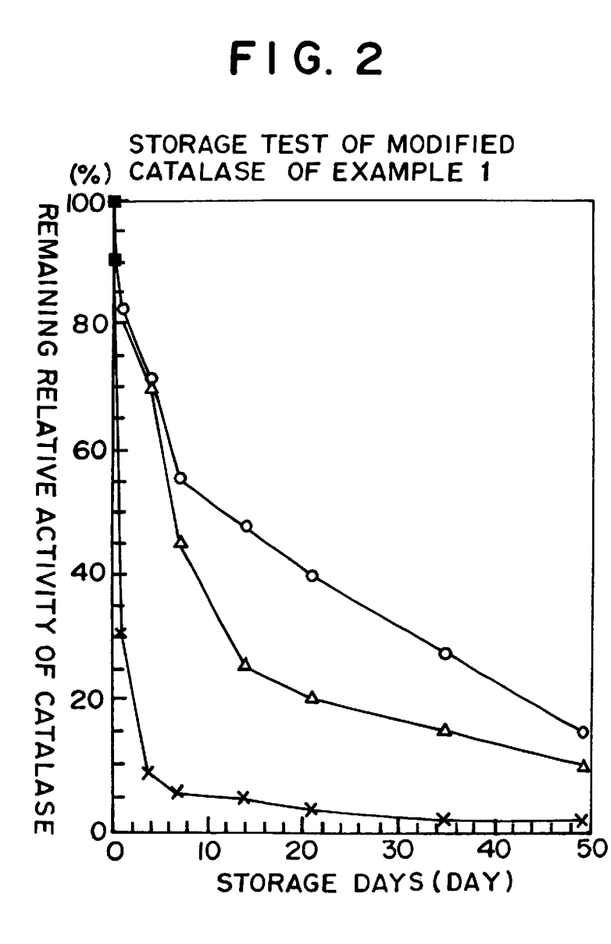
FIG. 2: Result of storage test of modified catalase of Example 1.

Results are shown in FIG. 2.

EXAMPLE 2

Catalase 5 g was dissolved in deionized water 100 g. The solution of catalase was adjusted to pH 7.0 by adding a 0.01 N aqueous sodium hydroxide solution and maintained at 3° C. Fine powder (10 g) of the copolymer (A) No. 2 obtained in the preparation example hereinbefore was added to the solution. The mixture was stirred at 3±1° C. for 30 minutes. Then, fine powder (5 g) of the copolymer (A) No. 2 obtained in the preparation example hereinbefore was added and stirred at the same temperature for 30 minutes. Water was distilled off at 25° C. in vacuo to obtain modified catalase 19.5 g.

Catalase activity of the obtained modified catalase was assayed to find that 1/3 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated.

Figure 3:
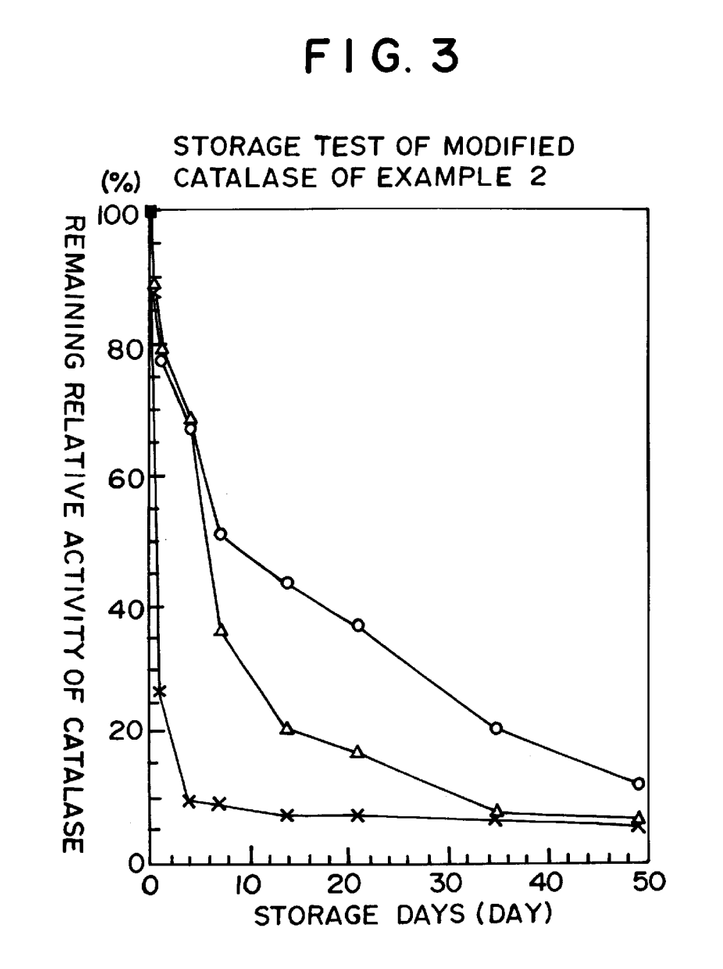
FIG. 3: Result of storage test of modified catalase of Example 2.

Results are shown in FIG. 3.

EXAMPLE 3

Catalase 5 g was dissolved in deionized water 100 g. A solution of catalase was adjusted to pH 7.5 by adding a 0.01 N aqueous sodium hydroxide solution and maintained at 3° C. The copolymer (A) No. 3 (5 g) obtained in the preparation example hereinbefore was added to the solution. The mixture was stirred at 3±1° C. for 30 minutes. Then, the copolymer (A) No. 3 (5 g) obtained in the preparation example hereinbefore was added and stirred at the same temperature for 30 minutes. Water was distilled off at 25° C. in vacuo to obtain modified catalase 13.8 g.

Activity of the obtained modified catalase was measured to find that 1/4 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 4:
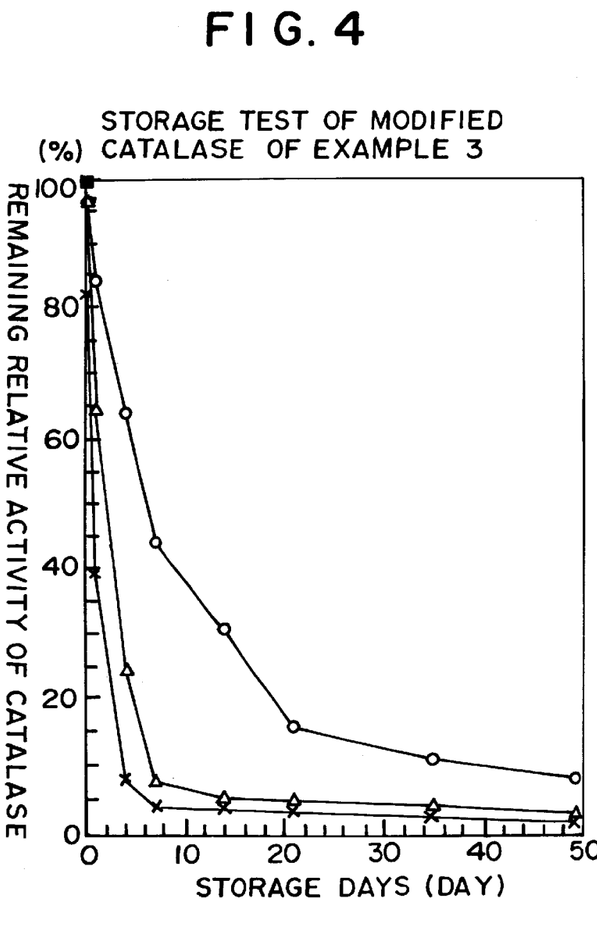
FIG. 4: Result of storage test of modified catalase of Example 3.

Results are shown in FIG. 4.

EXAMPLE 4

Catalase 5 g was dissolved in deionized water 100 g. A solution of catalase was adjusted to pH 7.5 by adding a 0.01 N aqueous sodium hydroxide solution and maintained at 3° C. The copolymer (A) No. 4 (10 g) obtained in the preparation example hereinbefore was added to the solution. The mixture was stirred at 3±1° C. for 30 minutes. Then, the copolymer (A) No. 4 (5 g) obtained in the preparation example hereinbefore was added and stirred at the same temperature for 30 minutes. Water was distilled off at 25° C. in vacuo to obtain modified catalase 18.3 g.

Activity of the obtained modified catalase was measured to find that 1/3 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 5:
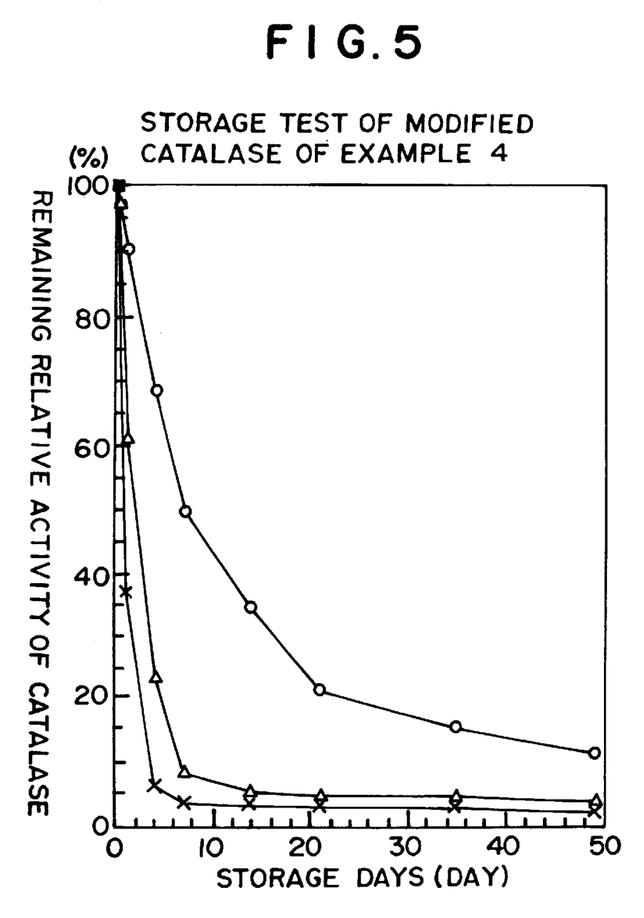
FIG. 5: Result of storage test of modified catalase of Example 4.

Results are shown in FIG. 5.

EXAMPLE 5

Catalase 5 g was dissolved in borate buffer, pH 9.0, 100 g, and the resulted solution of catalase was maintained at 3° C.

The copolymer (A) No. 5 (5 g) obtained in the preparation example hereinbefore was added to the catalase solution. The mixture was stirred at 3±1° C. for 30 minutes. Then, the copolymer (A) No. 5 (5 g) obtained in the preparation example hereinbefore was added and stirred at the same temperature for 30 minutes. Water was distilled off at 25° C. in vacuo to obtain modified catalase 14.3 g.

Activity of the obtained modified catalase was measured to find that 1/5 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 6:
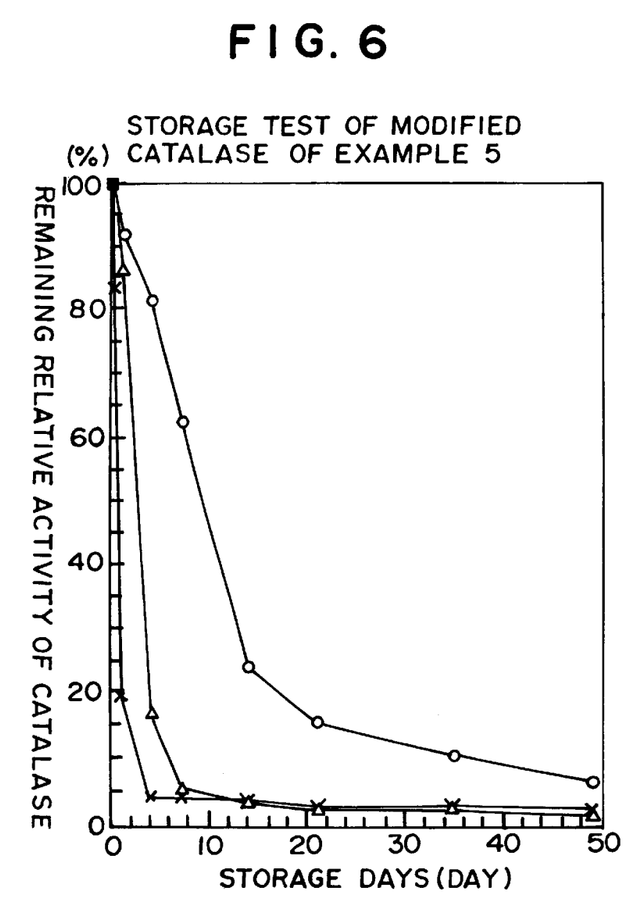
FIG. 6: Result of storage test of modified catalase of Example 5.

Results are shown in FIG. 6.

EXAMPLE 6

Catalase 5 g was dissolved in borate buffer, pH 9.0, 100 g, and the resulted solution of catalase was maintained at 3° C.

Fine powder (10 g) of the copolymer (A) No. 6 obtained in the preparation example hereinbefore was added to the solution. The mixture was stirred at 3±1° C. for 30 minutes.

Then, the fine powder (5 g) of the copolymer (A) No. 6 obtained in the preparation example hereinbefore was added and stirred at the same temperature for 30 minutes. Water was distilled off at 25° C. in vacuo to obtain modified catalase 19.2 g.

Activity of the obtained modified catalase was measured to find that 1/6 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 7:
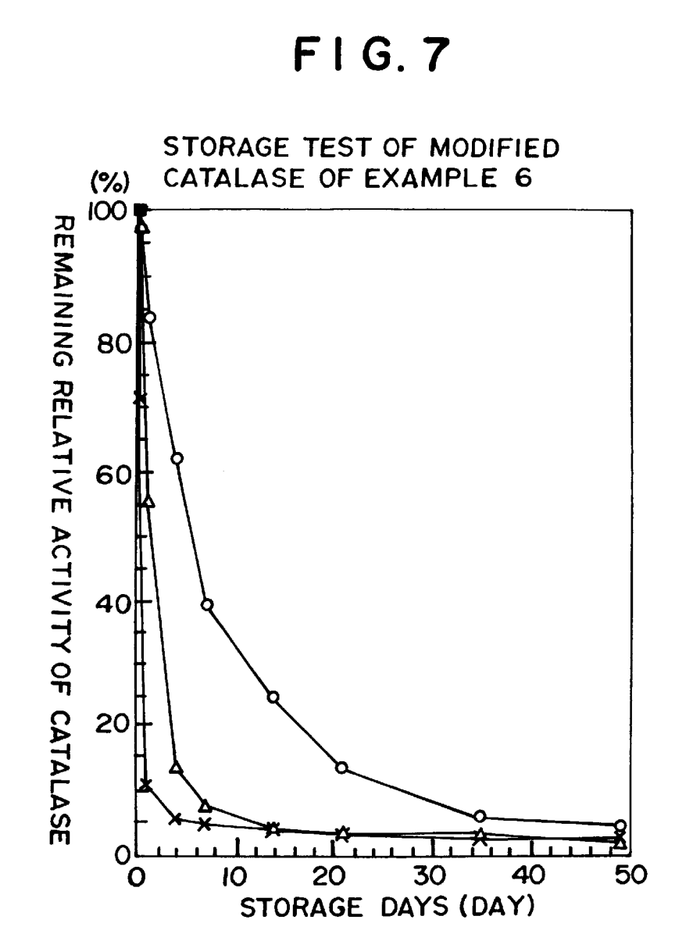
FIG. 7: Result of storage test of modified catalase of Example 6.

Results are shown in FIG. 7.

EXAMPLE 7

Catalase 5 g was dissolved in borate buffer, pH 9.0, 100 g, and the resulted solution of catalase was maintained at 3° C.

The copolymer (A) No. 7 (10 g) obtained in the preparation example hereinbefore was added to the solution. The mixture was stirred at 3±1° C. for 30 minutes. Then, the copolymer (A) No. 7 (5 g) obtained in the preparation example hereinbefore was added and stirred at the same temperature for 30 minutes. Water was distilled off at 25° C. in vacuo to obtain modified catalase 19.3 g.

Activity of the obtained modified catalase was measured to find that 1/4 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 8:
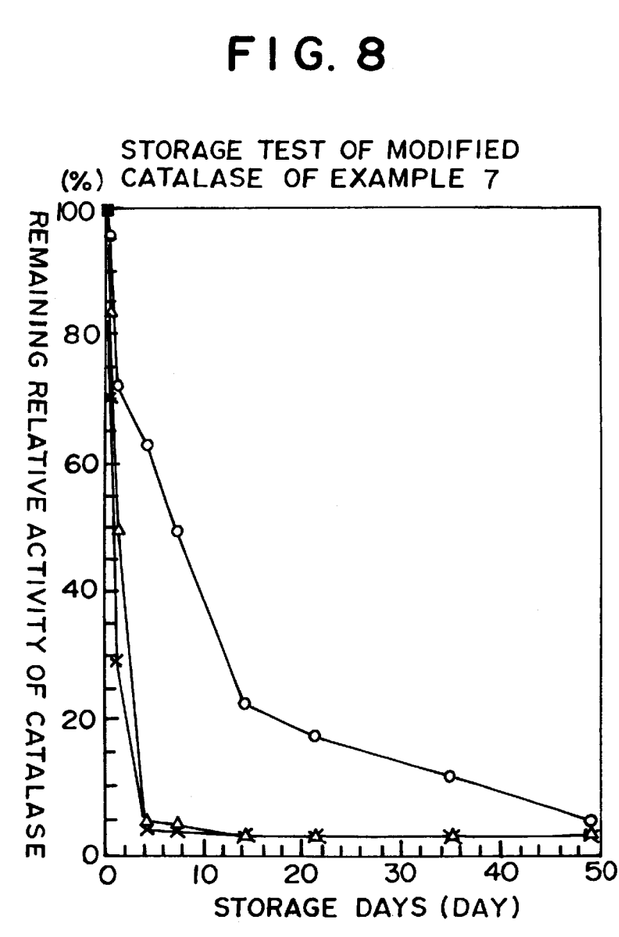
FIG. 8: Result of storage test of modified catalase of Example 7.

Results are shown in FIG. 8.

EXAMPLE 8

Catalase 5 g was dissolved in borate buffer, pH 9.0, 100 g, and the resulted solution of catalase was maintained at 3° C.

Fine powder (5 g) of the copolymer (A) No. 8 obtained in the preparation example hereinbefore was added to the solution. The mixture was stirred at 3±1° C. for 30 minutes. Then, fine powder (5 g) of the copolymer (A) No. 8 obtained in the preparation example hereinbefore was added and stirred at the same temperature for 30 minutes. Water was distilled off at 25° C. in vacuo to obtain modified catalase 14.3 g.

Activity of the obtained modified catalase was measured to find that 1/3 activity of the original catalase was maintained.

Homogeneous mixtures of the modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 9:
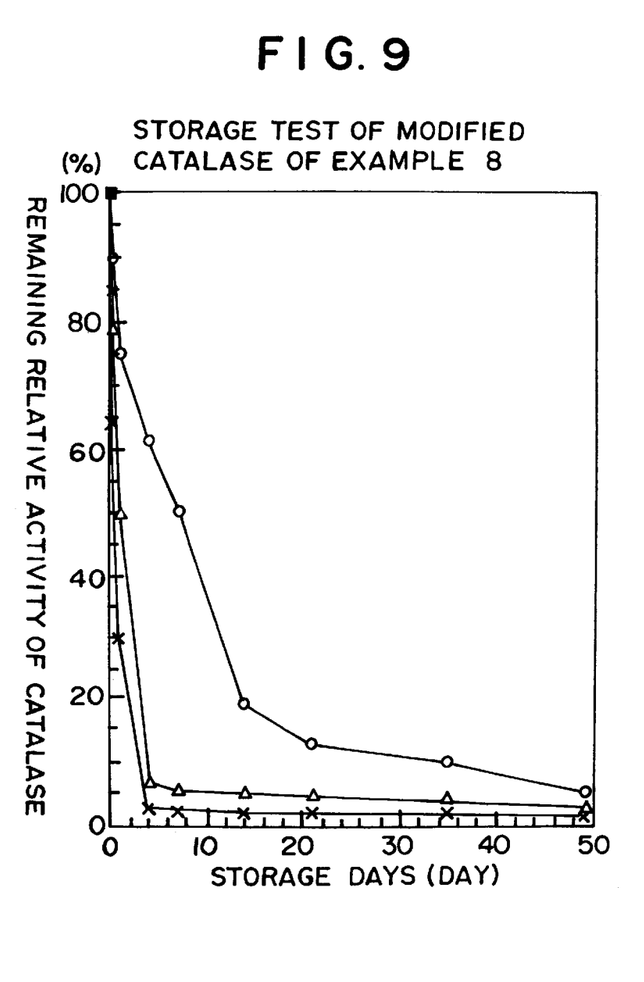
FIG. 9: Result of storage test of modified catalase of Example 8.

Results are shown in FIG. 9.

Results in FIG. 1 show that stabilities of unmodified catalase against peroxoacid salt at 30° C., 40° C. and 50° C. are very small. Results in FIG. 2 to FIG. 9 show that modified catalases of the present invention have stability for a long term against peroxoacid salts during the storage at 30° C., 40° C. or 50° C. This means excellent storage stability, especially at 30° C. and 40° C.

EXAMPLE 9

Catalase 5 g was dissolved in deionized water 100 g. A solution of catalase was adjusted to pH 7.0 by adding a 0.01 N aqueous sodium hydroxide solution and maintained at 3° C. The copolymer (A) No. 1 (10 g) obtained in the preparation example hereinbefore was added to the solution. The mixture was stirred at 3±1° C. for 30 minutes. Then, fine powder (5 g) of the copolymer (A) No. 2 obtained in the preparation example hereinbefore was added and stirred at the same temperature for 30 minutes to obtain modified catalase solution.

To the modified catalase solution was added the copolymer (B), which was aqueous solution of isobutylene-maleic anhydride copolymer prepared by dissolving isobutylene-maleic anhydride copolymer ("isoban-104", trade name, K. K. Kuraray, number average molecular weight $6.5-7.5 \times 10^4$) 10 g dissolved in deionized water 50 g. The mixture was stirred for 10 minutes. Water was distilled off at 25° C. in vacuo to obtain a composition of modified catalase 28.5 g.

Activity of the obtained composition of modified catalase was measured to find that 1/9 activity of the original catalase was maintained.

Homogeneous mixtures of the composition of modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 10:
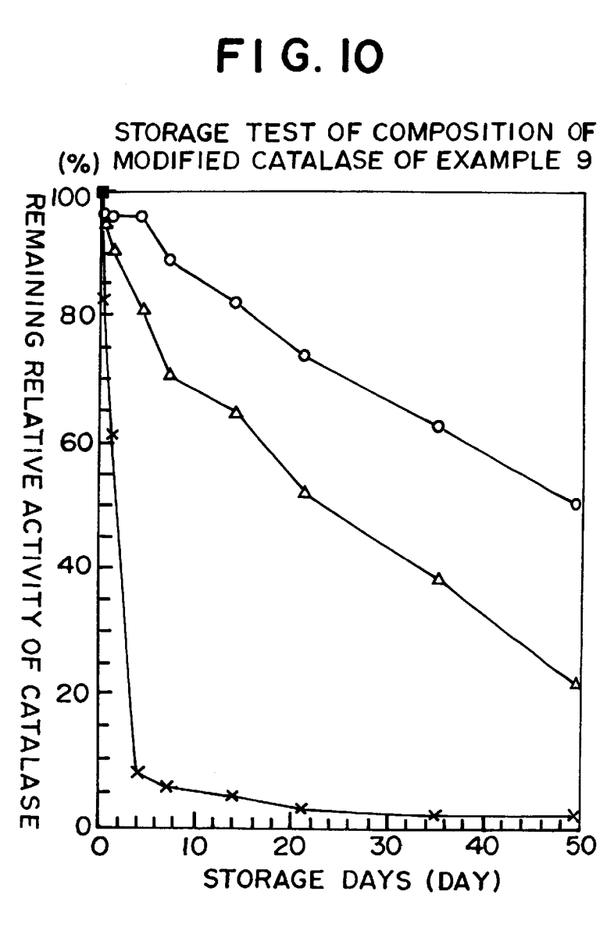
FIG. 10: Result of storage test of a composition of the modified catalase of Example 9

Results are shown in FIG. 10.

EXAMPLE 10

Catalase 5 g was dissolved in deionized water 100 g. A solution of catalase was adjusted to pH 7.0 by adding a 0.01 N aqueous sodium hydroxide solution and maintained at 3° C. Fine powder (10 g) of the copolymer (A) No. 2 obtained in the preparation example hereinbefore was added to the solution. The mixture was stirred at 3±1° C. for 30 minutes. Then, fine powder (5 g) of the copolymer (A) No. 2 obtained in the preparation example hereinbefore was added and stirred at the same temperature for 30 minutes to obtain a modified catalase solution.

To the modified catalase solution was added the copolymer (B), which was aqueous solution of isobutylene-maleic anhydride copolymer prepared by dissolving isobutylene-maleic anhydride copolymer ("isoban-104", trade name, K. K. Kuraray, number average molecular weight $6.5-7.5 \times 10^4$) 10 g dissolved in deionized water 50 g, and the mixture was stirred for 10 minutes. Water was distilled off at 25° C. in vacuo to obtain a composition of modified catalase 29.3 g.

Activity of the obtained composition of modified catalase was measured to find that 1/8 activity of the original catalase was maintained.

Homogeneous mixtures of the composition of modified catalase 100,000 units and sodium peroxocarbonate 100 g were stored in thermostats kept at 30° C., 40° C. and 50° C., respectively, for storage test. Catalase activities during the storage were assayed and remaining relative activities of catalase were calculated therefrom.

Figure 11:
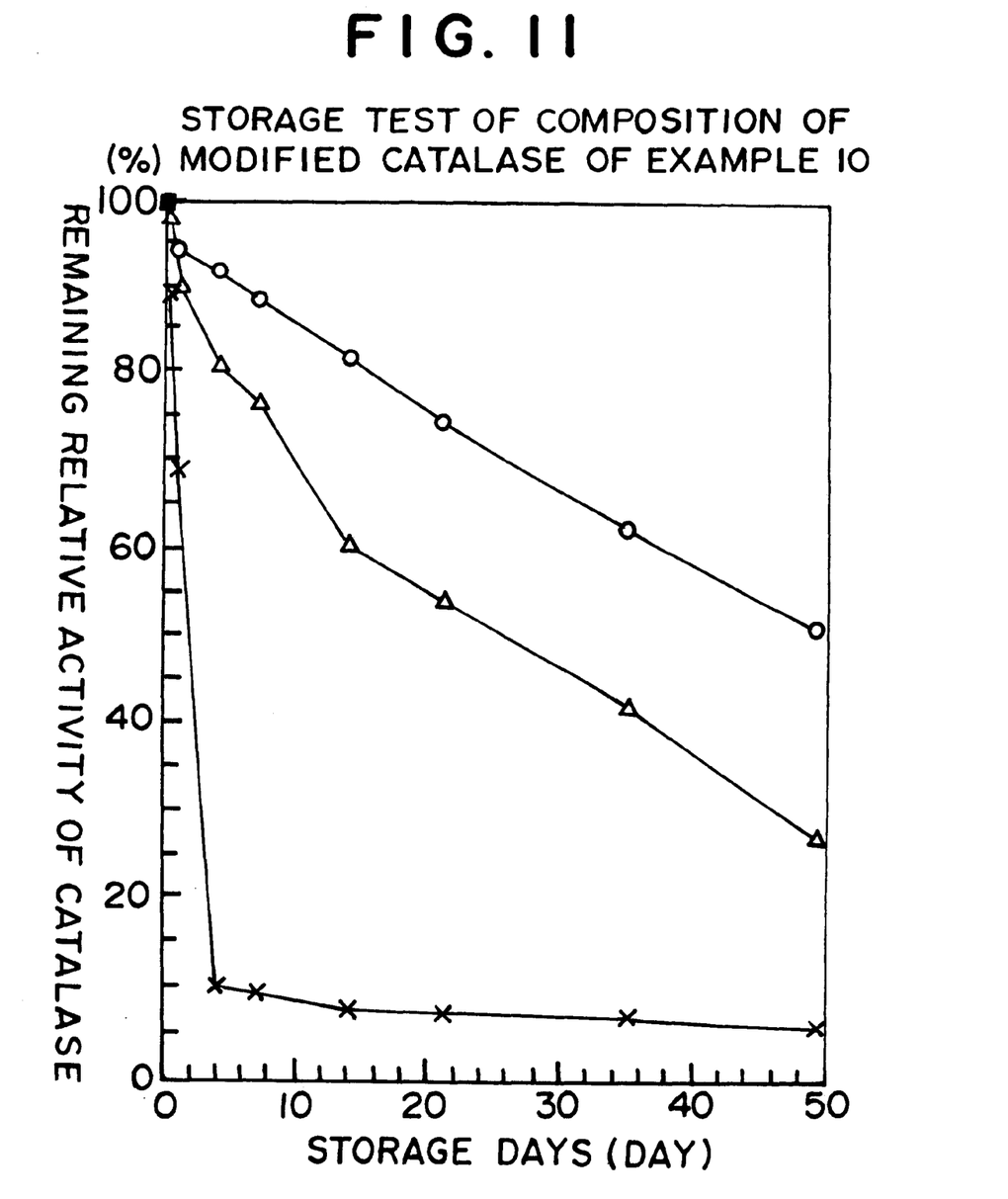
FIG. 11: Result of storage test of a composition of the modified catalase of Example 10.

Results are shown in FIG. 11.

Results in FIG. 10 and FIG. 11 show that the compositions of the modified catalase of the present invention have stability for a long term against peroxoacid salts during storage at 30° C., 40° C. and 50° C., respectively, especially excellent storage stability at 30° C. and 40° C. Furthermore, the storage stability of the composition of the modified catalase of the present invention is remarkably larger than that of the modified catalase of the present invention.

The modified catalase and the composition containing said modified catalase can easily be produced. Furthermore, it has increased long-term stability and storage stability against peroxoacid salts such as sodium peroxocarbonate as compared with that of catalase itself and the prior known modified catalases.

What we claim is:

1. A composition comprising a catalase modified with a copolymer (A) comprising:
   (a) one or more alkenyl ether of the formula (1) mentioned below,
   (b) maleic anhydride, and
   (c) at least on monomer selected from the group consisting of unsaturated carboxylic acid, vinyl compound and olefin,
wherein the above (a), (b) and (c) are 5–60:20–90:0–30 in molar ratio, respectively, and being stabilized against peroxoacid salt:

wherein Z is a residue of a compound having 2 to 8 hydroxyl group, AO is one or more oxyalkylene groups of 2 to 18 carbon atoms and may be in block or random addition when two or more of them are in addition at the same time, $R^1$ is an alkenyl group having 2 to 5 carbon atoms, $R^2$ is a hydrocarbon or acyl group having 1 to 24 carbon atoms, a and b are each 0 to 1000, m is 1 to 7 and a+bm is 1 to 1000,
   and a copolymer (B) consisting of an ethylenically unsaturated monomer and a monomer selected from the group consisting of a monomer having a carboxyl group and a monomer having an acid anhydride group, or a salt of the copolymer (B).

2. A composition of a modified catalase as in claim 1 wherein, in formula 1, $R^1$ is an alkenyl group having 3 to 4 carbon atoms, AO is an oxyalkylene group having 2 to 4 carbon atoms, and $R^2$ is a group selected from the groups consisting of hydrocarbon and acyl group having 1 to 4 carbon atoms.

3. A composition of a modified catalase as in claim 1 wherein, in the formula (1) of the alkenyl ether for the copolymer (A), the oxyalkylene groups AO contain at least 20% by weight of the oxyethylene group.

4. A composition of a modified catalase as in claim 2 wherein, in formula 1, of alkenyl ether for the copolymer A, the oxyalkylene groups AO contain at least 20% by weight of oxyethylene group.

5. A composition of a modified catalase according to claim 1 wherein the copolymer (B) is isobutylene-maleic anhydride copolymer having $5\times10^{-4}$ to $17\times10^4$ of number average molecular weight.

6. A composition of a modified catalase according to claim 2 wherein the copolymer (B) is isobutylene-maleic anhydride copolymer having $5\times10^{-4}$ to $17\times10^4$ of number average molecular weight.

7. A composition of a modified catalase according to claim 3 wherein the copolymer (B) is isobutylene-maleic anhydride copolymer having $5\times10^{-4}$ to $17\times10^4$ of number average molecular weight.

8. A composition of a modified catalase according to claim 4 wherein the copolymer (B) is isobutylene-maleic anhydride copolymer having $5\times10^{-4}$ to $17\times10^4$ of number average molecular weight.

9. A composition of a modified catalase according to claim 1 wherein the copolymer (B) is isobutylene-maleic anhydride copolymer having $5\times10-4$ to $17\times104$ of number average molecular weight and the copolymer A is 20 to 1000 parts by weight each 100 parts by weight of catalast.

10. A composition of a modified catalase according to claim 1 wherein the copolymer (B) is 0.1 to 1000 parts by weight each 100 parts by weight of the modified catalase.

11. A composition of a modified catalase according to claim 2 wherein the copolymer (B) is 0.1 to 1000 parts by weight each 100 parts by weight of the modified catalase.

12. A composition of a modified catalase according to claim 3 wherein the copolymer (B) is 0.1 to 1000 parts by weight each 100 parts by weight of the modified catalase.

13. A composition of a modified catalase according to claim 4 wherein the copolymer (B) is 0.1 to 1000 parts by weight each 100 parts by weight of the modified catalase.

14. A composition of a modified catalase according to claim 5 wherein the copolymer (B) is 0.1 to 1000 parts by weight each 100 parts by weight of the modified catalase.

15. A composition of a modified catalase according to claim 6 wherein the copolymer (B) is 0.1 to 1000 parts by weight each 100 parts by weight of the modified catalase.

16. A composition of a modified catalase according to claim 7 wherein the copolymer (B) is 0.1 to 1000 parts by weight each 100 parts by weight of the modified catalase.

17. A composition of a modified catalase according to claim 8 wherein the copolymer (B) is 0.1 to 1000 parts by weight each 100 parts by weight of the modified catalase.

18. A composition of a modified catalase according to claim 9 wherein the copolymer (B) is 0.1 to 1000 parts by weight each 100 parts by weight of the modified catalase.

19. A composition of a modified catalase according to claim 10 wherein the copolymer (B) is 0.1 to 1000 parts by weight each 100 parts by weight of the modified catalase.

* * * * *